United States Patent [19]

Gagnebien et al.

[11] Patent Number: 6,024,947
[45] Date of Patent: Feb. 15, 2000

[54] COSMETIC COMPOSITIONS HAVING IMPROVED RINSABILITY

[75] Inventors: Didier Gagnebien, Westfield, N.J.; Christian Felardos, Chevilly Larue, France

[73] Assignee: L'Oreal, Paris, France

[21] Appl. No.: 09/006,047

[22] Filed: Jan. 12, 1998

[30] Foreign Application Priority Data

Jan. 10, 1997 [FR] France ................................. 97-00213

[51] Int. Cl.$^7$ .................................. A61K 47/00
[52] U.S. Cl. ........................ 424/70.1; 424/401; 514/506; 514/529; 514/880; 514/881; 514/844; 514/847; 514/848; 514/937; 514/938; 514/944
[58] Field of Search .................................. 424/401, 70.1; 514/506, 529, 880, 881, 844, 847, 848, 937, 938, 944

[56] References Cited

U.S. PATENT DOCUMENTS

| | | | |
|---|---|---|---|
| 4,844,886 | 7/1989 | Hartmann et al. | 424/62 |
| 5,047,166 | 9/1991 | Weil | 252/132 |
| 5,089,531 | 2/1992 | Weil | 514/785 |
| 5,312,968 | 5/1994 | O'Lenick, Jr. et al. | 560/182 |
| 5,455,025 | 10/1995 | Pereira et al. | 424/59 |
| 5,597,555 | 1/1997 | Pereira et al. | 424/59 |

FOREIGN PATENT DOCUMENTS

| | | |
|---|---|---|
| 0 199v 131 | 10/1986 | European Pat. Off. . |
| 0 282 289 | 9/1988 | European Pat. Off. . |
| 0 521 647 | 1/1993 | European Pat. Off. . |
| 2 623 422 | 5/1989 | France . |

*Primary Examiner*—Jose G. Dees
*Assistant Examiner*—Michael A. Williamson
*Attorney, Agent, or Firm*—Oblon, Spivak, McClelland, Maier & Neustadt, P.C.

[57] ABSTRACT

The invention relates to cosmetic compositions of improved rinsability, comprising an oily phase and a citric acid ester corresponding to formula (I):

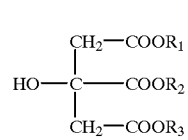

(I)

in which $R_1$, $R_2$ and $R_3$, which may be identical or different, represent a hydrogen atom, an alkali metal or alkaline-earth metal, an ammonium cation or a cation of an organic base or a group of formula (II):

$$-(C_nH_{2n}-O)_m-R_4 \qquad (II)$$

with n=2, 3 or 4 m=5–30 and $R_4$ represents a saturated, linear or branched $C_8$–$C_{24}$ alkyl group, at least one of $R_1$, $R_2$ and $R_3$ being a group of formula (II). These compositions are used in particular for cleansing and/or removing make-up from the skin.

5 Claims, No Drawings

COSMETIC COMPOSITIONS HAVING IMPROVED RINSABILITY

BACKGROUND OF THE INVENTION

1. Field of the Invention

The invention relates to novel oily cosmetic compositions having improved rinsability, as well as to the use of certain citric acid esters for improving the rinsability of oily compositions. The invention further relates to improving the rinsability of cleansing and/or make-up-removing compositions. As used herein, the term "rinsable" and "improved rinsability" means the invention composition is easily removed with water without leaving a residual film or greasy effect on the skin.

2. Discussion of the Background

Cleansing of the skin is very important for facial care, and should be of the highest possible performance since greasy residues such as excess sebum, residues of the cosmetic products used daily and make-up products, in particular "waterproof" products, accumulate in folds of the skin and on the skin surface and can obstruct the pores and lead to the appearance of spots. Poor quality cleansing, and in particular poor rinsing, are often responsible, among other causal factors, for a muddy complexion.

In the skin care field, cosmetically active agents are sometimes used in compositions intended to be rinsed out such as, for example, masks. Once they have been applied, such products are occasionally difficult to remove.

In the field of cleansing of the skin, the removal of "waterproof" make-up, transfer-free products and heavy make-up, such as theatrical make-up, require the use of oily compounds in order to be effective.

Although effective, known products, anhydrous oils and gels, creams and milks, are not without drawbacks.

Rinsable anhydrous oils and gels have a cleansing action by virtue of the oils contained in these formulations. These oils permit dissolution of the greasy residues and dispersion of the make-up pigments. These products are effective and well-tolerated. They have the drawback of being heavy, of not foaming and of not giving a sensation of freshness when they are applied, which is a penalty in cosmetic terms.

Make-up-removing creams and milks contain both oils, emulsifiers and detergent surfactants in an amount which is sufficiently low so as not to destabilize the emulsion. The rinsability of these products is insufficient, thus making it necessary to use a complementary detergent tonic lotion in order to improve the rinsing and the removal of soiling. Besides its astringent nature, the use of this second product can cause long-term drying of the skin.

It has been sought to design oily care, cleansing and/or make-up products which are of improved rinsability and totally harmless.

It is known, for example, from document EP-A-199,131, to use oxyethylenated partial esters of citric acid, and in particular their detergent properties, their foaming power and their biodegradability are known. However, the compositions of the prior art comprising these citric esters are aqueous, oil-free surfactant compositions comprising high levels of these citric esters. The use of these citric esters to improve the rinsability of oily cosmetic compositions is neither mentioned nor suggested.

Moreover, document EP-A-282,289 describes the incorporation of citric acid esters as softeners in cosmetic compositions. However, the compositions described are not rinsable cleansing compositions.

OBJECTS OF THE INVENTION

One object of the invention is to provide cosmetic compositions which can readily be rinsed off although they comprise an oily phase.

DETAILED DESCRIPTION OF THE INVENTION

A first preferred embodiment of the invention is a rinsable cosmetic composition comprising:

(i) at least one oily phase;

(ii) at least one citric acid ester corresponding to formula (I):

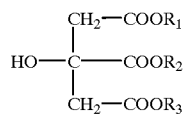

(1)

in which $R_1$, $R_2$ and $R_3$, which may be identical or different, represent a hydrogen atom, an alkali metal or alkaline-earth metal, an ammonium cation or a cation of an organic base or a group of formula (II):

(II)

with n=2, 3 or 4 m=5–30 and $R_4$ represents a saturated, linear or branched $C_8$–$C_{24}$ alkyl group, at least one of $R_1$, $R_2$ and $R_3$ being a group of formula (II).

The preparation of such products is well known to those skilled in the art. Reference may be made, for example, to document EP-A- b 199,131, incorporated herein by reference, in which syntheses of compounds corresponding to formula (I) are illustrated.

The group of formula (II) preferably comprises at least 5 ($C_nH_{2n}$—O) groups and more preferably at least 7 ($C_nH_{2n}$—O) groups.

Preferably, according to the invention, compounds corresponding to formula (I) are chosen in which:

n=2 or 3, m=7 to 20, and better still from 7 to 12, and/or $R_4$ represents a $C_{12}$–$C_{18}$ alkyl group.

Mixtures of compounds of formula (I) may be used.

Preferably, the compositions according to the invention are in the form of an oily lotion or an oily gel or an oil-in-water emulsion.

The advantages associated with the use of citric esters according to formula (I) are particularly noteworthy herein in compositions comprising a high oil content, that is to say at least 40% by weight of oil relative to the total weight of the composition and advantageously at least 50% oil, these compositions usually being difficult to rinse off. This effect is also particularly noteworthy in compositions comprising few surfactants, other than the invention citric acid ester, that is to say less than 5% by weight relative to the total weight of the composition, preferably less than 1% and even more preferably no surfactants at all, combined with a high oil content.

By virtue of these citric acid esters, the removal of "waterproof" make-up products and so-called "transfer-free" make-up products is made more comfortable insofar as it is possible:

to use oily compositions comprising fewer surfactants,
to rinse the oily composition lightly,
not to have an impression of heaviness on the skin after rinsing.

Additionally, the cleansing of and/or removal of make-up from sensitive skin is made comfortable, on account of the preferred low level or absence of surfactants in the compositions according to the invention and the high tolerance of the skin to citric esters.

The improvement in the rinsability of oily compositions by citric esters corresponding to formula (I) is all the more noteworthy since no similar effect has been seen with oxyethylenated phosphoric acid esters of fatty alcohols.

Oxyethylenated fatty acid esters of sorbitan only improve the rinsability of compositions comprising them at levels of greater than 10% by weight relative to the total weight of the oily composition. In addition, the oxyethylenated sorbitan esters having the greatest efficacy in this application are oxyethylenated oleic esters of sorbitan, which have the drawback of being very oxidizable. Their use consequently requires the joint use of high levels of antioxidants, which is not desirable in terms of the tolerance of the skin to these compositions. On the other hand, the citric acid esters according to formula (I) have such an effect at and above concentrations of 0.1% by weight relative to the total weight of the composition and are not oxidizable.

Preferably, the one or more citric esters of formula (I) are introduced into the invention compositions according to the invention at concentrations ranging from 0.5 to 10% by weight relative to the total weight of the composition, and even more preferably from 0.5 to 5%. The constituents of the oily phase can be chosen, alone or as mixtures, from various fatty substances, oils of plant, animal or mineral origin, natural or synthetic waxes, and the like.

Oils which can be used in the present invention include oils of plant or animal origin such as, for example, perhydrosqualene, squalane, coconut oil, macadamia oil, mink oil, turtle oil, soybean oil, grapeseed oil, sesame oil, corn oil, rapeseed oil, sunflower oil, cottonseed oil, avocado oil, olive oil, castor oil, jojoba oil, groundnut oil; hydrocarbon oils such as liquid paraffin, petroleum jelly; silicone oils such as polymethylsiloxanes, polymethylphenylsiloxanes, polysiloxanes modified with fatty acids, polysiloxanes modified with fatty alcohols, polysiloxanes modified with polyoxyalkylenes, fluorosilicones; perfluoro and/or organofluoro oils; higher fatty acids such as myristic acid, palmitic acid, stearic acid, behenic acid, oleic acid, linoleic acid, linolenic acid and isostearic acid, higher fatty alcohols such as cetanol, stearyl alcohol, oleyl alcohol; mono- and diesters, among which mention may be made in particular of isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, 2-diethylhexyl succinate, diisostearyl malate, 2-octyldodecyl lactate, glyceryl triisostearate, di-n-butyl adipate, bis(2-ethylhexyl) adipate, ethylene glycol dioleate, ethylene glycol diisotridecanoate, ethylene glycol diisostearate, neopentyl glycol dicaprylate.

Needless to say, the fatty phase can also contain one or more standard lipophilic cosmetic adjuvants.

Preferably, at least one polar oil is contained in the oily phase, this oil contributing to the solubilization of the citric ester in the oily composition. Among the polar oils which can be used in the present invention, mention may be made of: triglycerides, benzoic acid esters, fatty esters of polyol. Advantageously, this polar oil represents at least 25% by weight relative to the total weight of the oily phase.

The compositions according to the invention can also comprise any usual ingredient well known to those skilled in the art, such as preserving agents, gelling agents, thickeners, antioxidants, fragrances, screening agents, dyestuffs, and hydrophilic or lipophilic active agents.

Advantageously, the invention relates to compositions for cleansing and/or removing make-up from the skin.

A subject of the invention is also the use of citric acid esters according to formula (I) in order to improve the rinsability of oily cosmetic compositions. This use essentially includes two preferred embodiments:

in oily compositions according to the invention as described above, or in aqueous rinsing lotions or tonic lotions used in combination with an oily cosmetic composition.

According to this second embodiment, the citric ester corresponding to formula (I) is preferably introduced in amounts ranging from 0.1% to 10% by weight relative to the total weight of the lotion, and preferably from 0.5 to 5%. In addition, such a lotion can comprise any usual ingredient which is well known to those skilled in the art, such as preserving agents, antioxidants, fragrances, screening agents, dyestuffs and hydrophilic or lipophilic active agents. Kits according to the second embodiment make up part of the invention.

Advantageously, less than 5%, more advantageously less than 1% and preferably no surfactants at all are introduced along with the citric acid ester according to (I) into this lotion, which makes it possible to have good rinsability without the disadvantages associated with the usual surfactants, including irritation and drying of the skin.

The oily cosmetic compositions intended to be rinsed off with such lotions advantageously satisfy the characteristics described above for oily compositions (oily gels, oily lotions or oil-in-water emulsions) according to the invention without, however, these oily compositions necessarily containing citric acid esters.

According to this second embodiment, the user cleanses and/or removes make-up from his or her skin using the oily composition, after which, in a second stage, rinsing of the skin is completed using the citric ester lotion.

EXAMPLES

In the examples all the percentages are given as weight of active material relative to the total weight of the composition.

EXAMPLE 1 make-up-removing oil

| | |
|---|---|
| Castor oil | 29% |
| 2-Ethylhexyl palmitate | 70% |
| Oxyethylenated citric monoester of coconut alcohol (9EO) | 1% |

EXAMPLE 2 make-up-removing product for the lips

| | |
|---|---|
| Castor oil | 40% |
| 2-Ethylhexyl palmitate | 54% |
| Oxyethylenated citric monoester of coconut alcohol (7EO) | 1% |
| Ethyl alcohol | 5% |

EXAMPLE 3
make-up-removing emulsion

| | |
|---|---|
| 2-Ethylhexyl palmitate | 60% |
| Xanthan gum | 1% |
| Oxyethylenated citric diester of coconut alcohol (9EO) | 1% |
| Preserving agent | 0.5% |
| Demineralized water qs | 100% |

The compositions of Examples 1 to 3 make it possible to obtain efficient and very gentle removal of make-up from the skin without the additional use of a lotion comprising surfactants being necessary.

French patent application 97 00213 is incorporated herein by reference.

What is claimed as new and is desired to be secured by Letters Patent of the United States is:

1. A method of improving the rinsability of an oily cosmetic composition, comprising adding to said composition at least one citric ester according to formula (I):

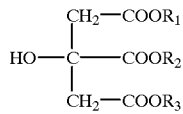

(I)

in which $R_1$, $R_2$ and $R_3$, which may be identical or different, represent a hydrogen atom, an alkali metal or alkaline-earth metal, an ammonium cation or a cation of an organic base or a group of formula (II):

$$-(C_nH_{2n}-O)_m-R_4 \qquad (II)$$

where n=2, 3 or 4; m=5–30; and $R_4$ represents a saturated, linear or branched $C_8$–$C_{24}$ alkyl group, at least one of $R_1$, $R_2$ and $R_3$ being a group of formula (II); and wherein the citric ester of formula (I) is introduced into an aqueous rinsing lotion or a tonic lotion, combined with the oily cosmetic composition.

2. The method according to claim 1, wherein the lotion comprises less than 5% by weight, relative to the total weight of the composition of surfactants other than the citric acid ester according to formula (I).

3. The method according to claim 1, wherein the lotion comprises from 0.1% to 10% by weight, relative to the total weight of the lotion, of at least one citric ester corresponding to formula (I).

4. The method according to claim 1, wherein: n is 2 or 3; m is 7 to 20; and $R_4$ represents a $C_{12}$–$C_{18}$ alkyl group.

5. The method according to claim 1, wherein m is 7 to 12.

* * * * *